(12) United States Patent
Oka

(10) Patent No.: US 7,846,523 B2
(45) Date of Patent: Dec. 7, 2010

(54) LAMINATED BODY WITH RELEASING MEMBER AND METHOD FOR MANUFACTURING THE SAME

(75) Inventor: Keiji Oka, Omihachiman (JP)

(73) Assignee: Piac Co., Ltd., Omihachiman-Shi, Shiga (JP)

( * ) Notice: Subject to any disclaimer, the term of this patent is extended or adjusted under 35 U.S.C. 154(b) by 644 days.

(21) Appl. No.: 11/795,296

(22) PCT Filed: Feb. 23, 2006

(86) PCT No.: PCT/JP2006/303236
§ 371 (c)(1),
(2), (4) Date: Sep. 5, 2007

(87) PCT Pub. No.: WO2006/098126
PCT Pub. Date: Sep. 21, 2006

(65) Prior Publication Data
US 2008/0131642 A1  Jun. 5, 2008

(30) Foreign Application Priority Data
Mar. 14, 2005 (JP) .............................. 2005-070432

(51) Int. Cl.
*B32B 9/00* (2006.01)
*B32B 33/00* (2006.01)
*B32B 7/12* (2006.01)
*B32B 15/04* (2006.01)

(52) U.S. Cl. .................. 428/40.1; 428/41.9; 428/195.1; 428/343; 428/353; 428/354

(58) Field of Classification Search ................ 428/40.1, 428/41.9, 42.1, 42.2, 42.3, 195.1, 343, 353, 428/354
See application file for complete search history.

(56) References Cited

U.S. PATENT DOCUMENTS 5,888,606 A * 3/1999 Senoo et al. ................ 428/66.6

FOREIGN PATENT DOCUMENTS

| JP | S63-172422 U | 11/1988 |
|----|--------------|---------|
| JP | H10-314214 A | 12/1998 |
| JP | 2003-190204 A | 7/2003 |

* cited by examiner

*Primary Examiner*—Patricia L Nordmeyer
(74) *Attorney, Agent, or Firm*—Manabu Kanesaka

(57) ABSTRACT

A medical laminated body with a releasing member, has a medical sticking member having a sequentially laminated base material and a pressure-sensitive adhesive layer. It further has a releasing member laminated on a side of the medical sticking member that is provided with the pressure-sensitive adhesive layer, and a repositionable pressure-sensitive adhesive layer formed as a part of the releasing member at a side of the releasing member distal from the medical sticking member. A ratio represented by A2/A1 is in a range of 8 to 100 where A1 is an adhesion of the repositionable pressure-sensitive adhesive layer in accordance with JIS-Z-0237 and A2 is an adhesion of the pressure-sensitive adhesive layer in accordance with JIS-Z-0237. A1 is in the range of 10 to 150 g/25 mm, and A2 is in the range of 250 to 1,000 g/25 mm.

13 Claims, 14 Drawing Sheets

Fig.4
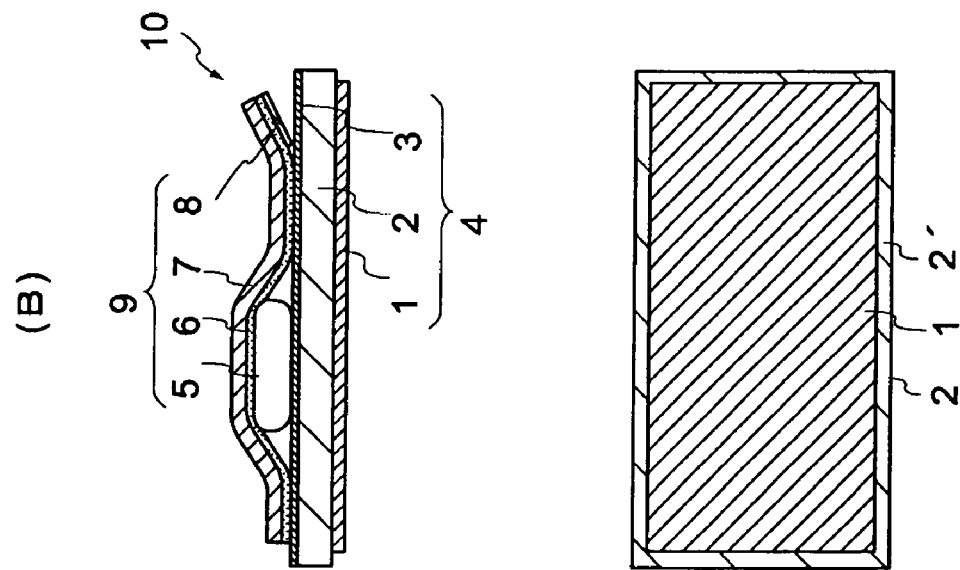
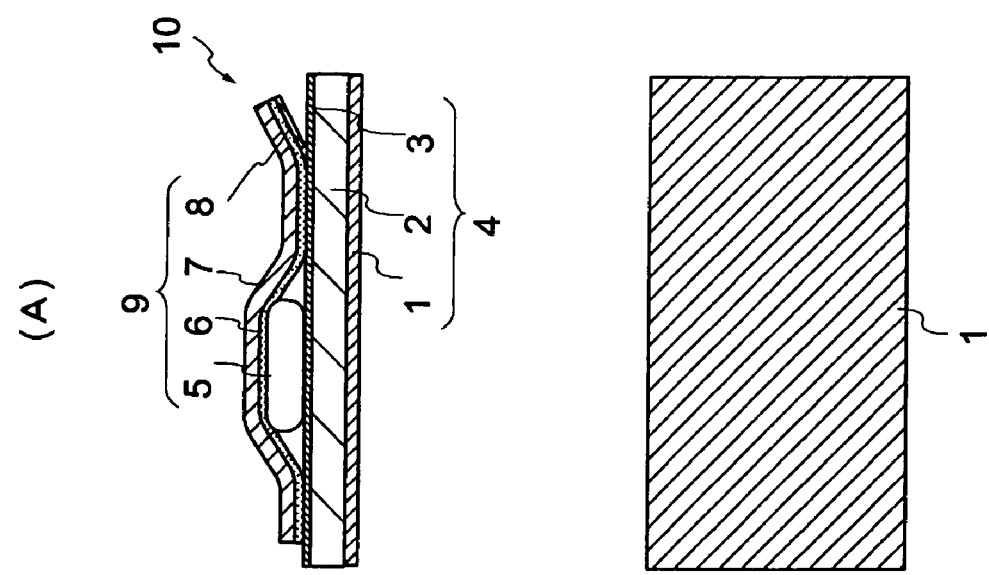

Fig.6
(A) 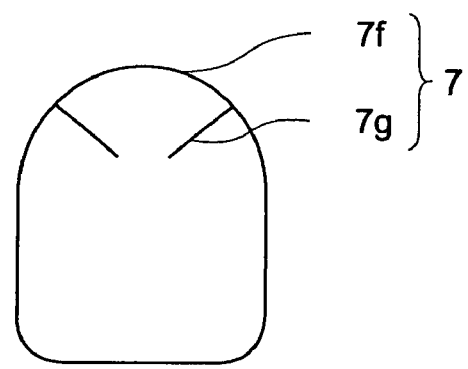
(B) 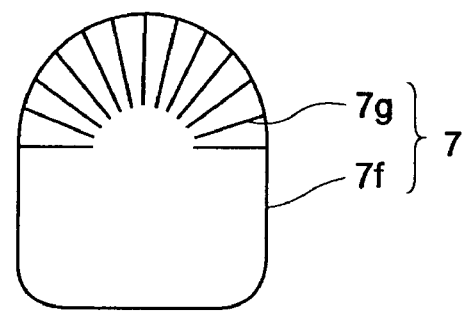
(C) 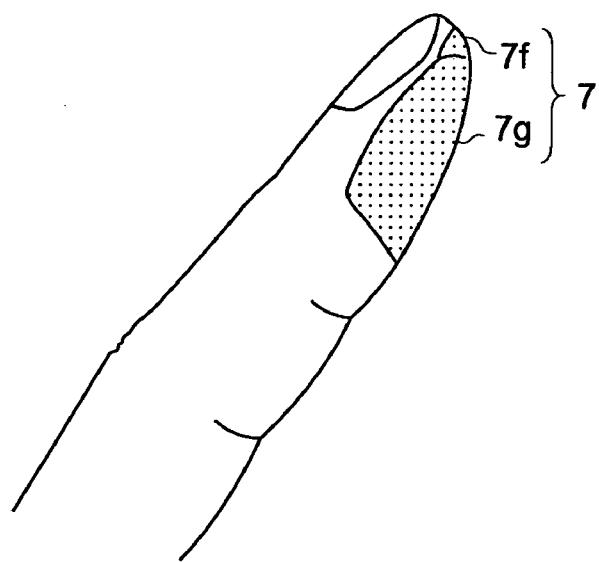

Fig.7
(A) 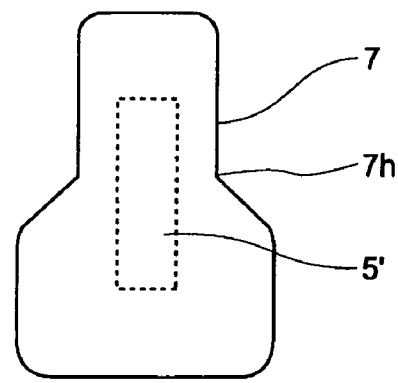
(B) 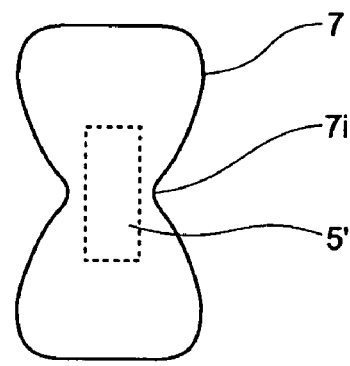
(C) 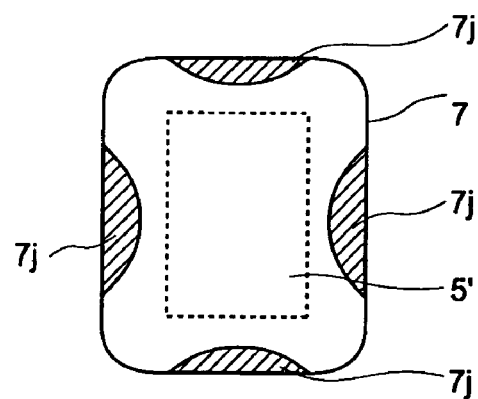
(D) 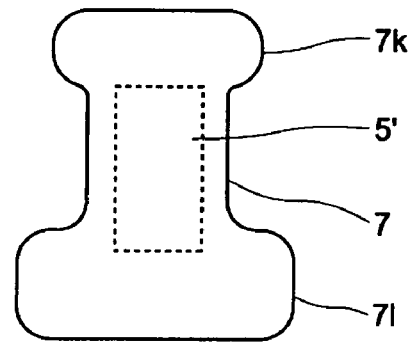

LAMINATED BODY WITH RELEASING MEMBER AND METHOD FOR MANUFACTURING THE SAME

BACKGROUND OF THE INVENTION

1. Field of the Invention

The present invention relates to a laminated body with a releasing member and a method for manufacturing the same, and in particular to a laminated body with a releasing member excellent not only in usability but also in a packaging property and a method for manufacturing the same.

2. Description of the Related Art

Conventionally, an adhesive plaster for injection and a medical adhesive material which are excellent in usability have been known.

As shown in FIG. 13, an adhesive plaster for injection 57, for example, is known (see, for example, patent document 1). The adhesive plaster for injection 57 is constituted as follows. A pressure-sensitive adhesive part 53 is formed on the backside of a base material 51 except for a non-sticking part 52 along one side of the base material 51. In addition, a plurality of pads 54 are stuck to the pressure-sensitive adhesive part 53 at predetermined intervals along the non-sticking part 52, while the whole region on the backside of the base material 51 is covered with the surface of a releasing film 55. Then, a plurality of cutting lines (not shown) are formed in the base material 51 so as to allow the pads 54 to be separated from one another, and a fixing pressure-sensitive adhesive part 58 is formed on the backside of the releasing film 55.

That is, the fixing pressure-sensitive adhesive part is formed on the backside of the releasing film, so that the backside of the releasing film can be fixed by sticking the fixing pressure-sensitive adhesive part to a suitable fixing part, and the operation of peeling off the base material from the surface of the releasing film can be performed with one hand. For this reason, a series of operations from release of the base material to attachment the pad to the skin can be achieved with one hand.

As shown in FIG. 14, a medical adhesive material is known (see, for example, patent document 2). The medical adhesive material is formed in such a manner that one side of a belt-shaped base material 101 is provided with a pressure-sensitive adhesive layer, several pads 103 are placed on determined positions of the pressure-sensitive adhesive layer at predetermined intervals along the belt, and a picking piece 104 is stuck such that the pressure-sensitive adhesive layer in one edge of the belt-shaped base material 101 is covered with the picking piece 104.

More specifically, a releasing film 106 is temporarily fixed onto the pad 103 and the pressure-sensitive adhesive layer not covered with the picking piece 104, thereby covering them with the releasing film. Then, cutting lines 108 for cutting the base material 101, the picking piece 104 and the releasing film 106 are arranged among the pads 103 but not on a linking part 107 on the releasing film 106 to thereby continuously form a plurality of sticking pieces 110. Accordingly, the picking piece 104 can be picked to peel off the pulling sticking piece 110 from the releasing film 106 and to stick the pad to an affected area. When the pad becomes unnecessary, the picking piece 104 can be picked to peel off it from the affected area and discarded.

In the adhesive plaster for injection disclosed in patent document 1, however, a strong fixing pressure-sensitive adhesive part is arranged on the backside of the releasing film, and the relationship between the adhesion (A1') of the fixing pressure-sensitive adhesion part and the adhesion (A2') of the pressure-sensitive adhesive layer is not taken into consideration. Accordingly, there is a problem that when the base material is to be peeled off from the surface of the releasing film, the releasing film with the base material still remaining thereon is peeled off from the fixing part, or the releasing film from which the base material has been peeled off is hardly peeled off from the fixing part. The adhesive plaster for injection disclosed in document 1 has another problem that because the strong fixing pressure-sensitive adhesive part is arranged on the backside of the releasing film, a plurality of such adhesive plasters for injection cannot be packaged by stacking them as they are.

On the other hand, the medical adhesive material disclosed in patent document 2 is provided with a pulling means for a sticking piece, thus improving the usability of the adhesive material, but cannot be easily peeled off with one hand.

[Patent document 1] JP-A-H10-314214 (claims)
[Patent document 2] JP-A 2003-190204 (claims)

SUMMARY OF THE INVENTION

Under these circumstances, the present inventors made extensive study, and as a result, they have found that by considering the adhesion (A1) of a repositionable pressure-sensitive adhesive layer and the adhesion (A2) of a pressure-sensitive adhesive layer in a laminated body with a releasing member, a sticking member when peeled off from the surface of the releasing member (releasing film) can be easily peeled off with one hand, while the releasing member from which the sticking member has been peeled off can also be easily peeled off with one hand.

The present inventors have also found that even if a plurality of such laminated body with a releasing member are packaged by stacking them as they are, each laminated body can be easily peeled off and used as a single laminated body with a releasing member, to thereby complete the present invention.

That is, an object of the present invention is to provide a laminated body with a releasing member excellent not only in usability but also in packaging property and a method for manufacturing the laminated body with a releasing member.

According to the present invention, there can be provided a laminated body with a releasing member, which includes a sticking member constituted by sequentially laminating a base material and a pressure-sensitive adhesive layer, wherein a releasing member is laminated on the side of the sticking member that is provided with the pressure-sensitive adhesive layer, and a repositionable pressure-sensitive adhesive layer is formed as a part of the releasing member at the backside of the releasing member. In the laminated body, a ratio represented by A2/A1 is a value in the range of 1.5 to 100 where A1 is the adhesion of the repositionable pressure-sensitive adhesive layer in accordance with JIS-Z-0237 and A2 is the adhesion of the pressure-sensitive adhesive layer in accordance with JIS-Z-0237. With the arrangement, the problem described above can be solved.

By constituting the laminated body in this way, the sticking member can be easily peeled off with one hand, while the releasing member from which the sticking member has been peeled off can also be easily peeled off with one hand. Even if a plurality of such laminated body with a releasing member are packaged by staking them as they are, each laminated body can be easily peeled off from one another and used as a single laminated body with a releasing member.

The adhesion (A1) of the repositionable pressure-sensitive adhesive layer in accordance with JIS-Z-0237 is measured as the adhesion thereof to a SUS plate, which is a value correlated sufficiently with the adhesion of the laminated body with a releasing member to a substrate (e.g., a wooden table or a steel table). Similarly, the adhesion (A2) of the pressure-sensitive adhesive layer in accordance with JIS-Z-0237 is measured as the adhesion thereof to a SUS plate, which is also a value correlated sufficiently with the adhesion of the laminated body with a releasing member to the releasing member (peel layer). Accordingly, a laminated body with a releasing member which is not only excellent in usability but also excellent in packaging property can be provided by regulating the ratio represented by A2/A1 in a predetermined range.

In constituting the laminated body with a releasing member according to the present invention, it is preferable that the adhesion (A1) of the repositionable pressure-sensitive adhesive layer in accordance with JIS-Z-0237 is a value in the range of 10 to 150 g/25 mm, while the adhesion (A2) of the pressure-sensitive adhesive layer in accordance with JIS-Z-0237 is a value in the range of 250 to 1,000 g/25 mm.

By specifically defining the adhesion (A1 and A2), a laminated body with a releasing member further excellent in usability and packaging property can be efficiently provided.

In constituting the laminated body with a releasing member according to the present invention, it is preferable that the repositionable pressure-sensitive adhesive layer is formed wholly on the other side of the releasing member or partially on that side excluding, for example, a portion within 15 mm from one edge of the releasing member.

When the repositionable pressure-sensitive adhesive layer is wholly formed, the adhesion ratio represented by A2/A1 can be easily regulated.

On the other hand, when the repositionable pressure-sensitive adhesive layer is partially formed, that is, when a part where the repositionable pressure-sensitive adhesive layer is not formed is arranged, the part facilitates release. It follows that when the sticking member is to be peeled off from the surface of the sticking member, the part where the repositionable pressure-sensitive adhesive layer is not formed can be utilized to peel off the sticking member easily and reliably with one hand.

In the case that the repositionable pressure-sensitive adhesive layer is partially formed, the releasing member from which the sticking member has been peeled off can also be utilized to facilitate release, and thus the releasing member can be peeled off easily and reliably by only one hand.

In the case that the repositionable pressure-sensitive adhesive layer is partially formed, a plurality of laminated body with a releasing member, even when packaged by stacking them as they are, can be easily separated into individual laminated body with a releasing member by utilizing the part where the repositionable pressure-sensitive adhesive layer is not formed.

When the repositionable pressure-sensitive adhesive layer is formed along the one edge, production of the laminated body is not made particularly difficult even if the part where the repositionable pressure-sensitive adhesive layer is not formed is arranged.

In constituting the laminated body with a releasing member according to the present invention, it is preferable that a pad portion is arranged on the surface of the pressure-sensitive adhesive layer in the sticking member.

With the constitution, the laminated body can be provided more preferably as, for example, a medical adhesive plaster or an adhesive plaster for injection.

In the case of a medical adhesive plaster or an adhesive plaster for injection, a nurse etc. should sometimes handle a plurality of medical adhesive plasters or adhesive plasters for injection and simultaneously conduct another operation. In this case, use of the laminated body with a releasing member excellent in usability and packaging property as disclosed based on the present invention is very meaningful.

In constituting the laminated body with a releasing member according to the present invention, it is preferable that the glass transition point of a repositionable pressure-sensitive adhesive constituting the repositionable pressure-sensitive adhesive layer is a value in the range of −20 to −60° C.

By constituting the laminated body in this manner, the releasing member from which the sticking member has been peeled off can be easily peeled off with one hand, even at a usage environment temperature in the range of low to high temperatures, for example −10 to 40° C., while there is less fear of deposit of the repositionable pressure-sensitive adhesive on the fixing portion to which the repositionable pressure-sensitive adhesive layer adheres.

In constituting the laminated body with a releasing member according to the present invention, it is preferable that the repositionable pressure-sensitive adhesive layer is a discontinuous layer whose lower layer is exposed in the plane direction.

With this constitution, the releasing member from which the sticking member has been peeled off can be easily peeled off with one hand, even at a usage environment temperature in the broader range of low to high temperatures, while there is less fear of deposit of the repositionable pressure-sensitive adhesive on the fixing portion.

In constituting the laminated body with a releasing member according to the present invention, it is preferable that a primer layer is arranged between the repositionable pressure-sensitive adhesive layer and the releasing member.

By constituting the laminated body in this way, the adhesion (A1) of the repositionable pressure-sensitive adhesive layer can be easily regulated, and consequently, the range of choice for the adhesion (A2) of the pressure-sensitive adhesive layer can also be broadened.

In constituting the laminated body with a releasing member according to the present invention, it is preferable that a picking piece is arranged between the releasing member and the sticking member.

The laminated body with a releasing member constituted by arranging a picking piece can be provided more preferably, for example, as a medical adhesive plaster or an adhesive plaster for injection.

In constituting the laminated body with a releasing member according to the present invention, it is preferable that the base material is provided with a cutting line along which the base material is cut in a predetermined shape.

The laminated body with a releasing member constituted in this manner can be made more excellent in usability and provided preferably, for example, as a medical adhesive plaster or an adhesive plaster for injection.

Another aspect of the invention is a method for manufacturing a laminated body with a releasing member, which includes a sticking member constituted by sequentially laminating a base material and a pressure-sensitive adhesive layer, wherein a releasing member is laminated on the side of the sticking member that is provided with the pressure-sensitive adhesive layer, and a repositionable pressure-sensitive adhesive layer is formed as a part of the releasing member at the backside of the releasing member, the method including the steps of: forming a repositionable pressure-sensitive adhesive layer on one side of the releasing member; and laminating a base material and a pressure-sensitive adhesive on the other side of the releasing member. In the method, a ratio represented by A2/A1 is allowed to be a value in the range of 1.5 to 100 where A1 is the adhesion of the repositionable pressure-sensitive adhesive layer in accordance with JIS-Z-0237 and A2 is the adhesion of the pressure-sensitive adhesive layer in accordance with JIS-Z-0237.

By this implementation, the sticking member and the releasing member can be easily peeled off with one hand. Even if a plurality of such laminated body with a releasing member are packaged by stacking them as they are, the laminated body with a releasing member can be easily peeled off from one another to efficiently give individual laminated body with a releasing member.

BRIEF DESCRIPTION OF THE DRAWINGS

FIGS. 4A and 4B are sectional and plan views of a laminated body with a releasing member having a repositionable pressure-sensitive adhesive layer laminated wholly, or wholly except for the peripheral part.

FIGS. 6A to 6C show a modification (No. 2) of the laminated body with a releasing member according to the present invention.

FIGS. 7A to 7D show a modification (No. 3) of the laminated body with a releasing member according to the present invention.

DESCRIPTION OF THE PREFERRED EMBODIMENTS

First Embodiment

Figure 1:
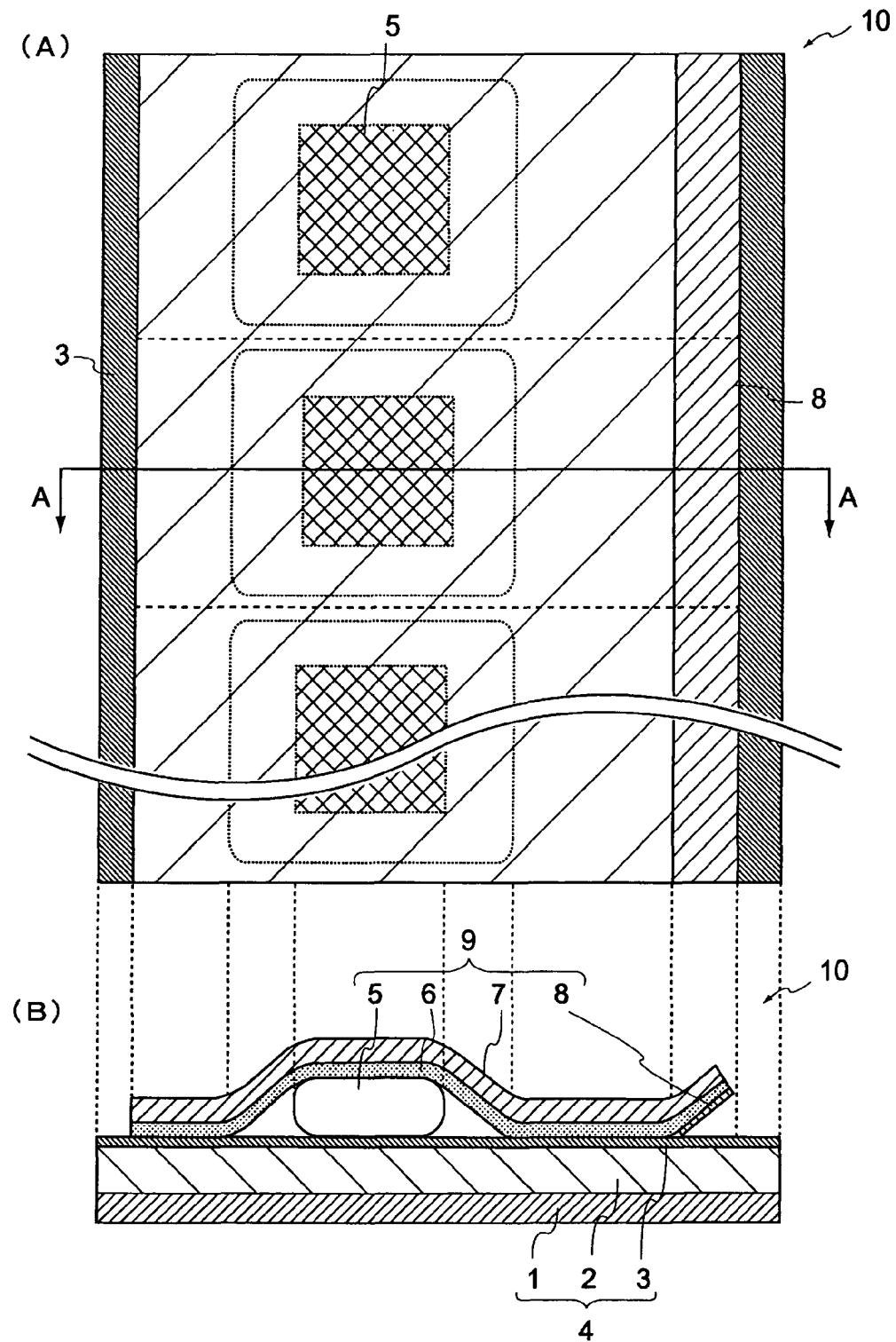
FIGS. 1A and 1B are respectively plan and sectional views (A-A line) of a laminated body with a releasing member according to the present invention.

As shown in FIGS. 1A and 1B, the first embodiment is a laminated body 10 with a releasing member, which includes a sticking member 9 constituted by sequentially laminating a base material 7 and a pressure-sensitive adhesive layer 6, and in which a releasing member 4 is laminated on the side of the sticking member 9 that is provided with the pressure-sensitive adhesive layer 6, and a repositionable pressure-sensitive adhesive layer 1 is formed as a part of the releasing member 4 at the backside of the releasing member 4, wherein a ratio represented by A2/A1 is a value in the range of 1.5 to 100 where A1 is the adhesion of the repositionable pressure-sensitive adhesive layer in accordance with JIS-Z-0237 and A2 is the adhesion of the pressure-sensitive adhesive layer in accordance with JIS-Z-0237.

1. Releasing Member (1) Type

Examples of the other part of the releasing member 4 than the repositionable pressure-sensitive adhesive layer 1, shown in FIG. 1B, include a silicone-based releasing film, a fluorine resin-based releasing film, a silicone-based peel paper, a fluorine resin-based peel paper, a polyethylene laminated paper, a polyethylene resin-based film, a polypropylene resin-based film, a polyester resin-based film, an acrylic resin-based film, a polycarbonate resin-based film, and a polyurethane resin-based film, and these materials can be used alone or as a combination of two or more thereof.

Accordingly, examples of the peel base material 2 constituting a part of the releasing member 4 include a paper, an impregnated paper, a polyester resin, a polycarbonate resin, a polypropylene resin, a polyethylene resin, a polyamide resin, an acrylic resin, a vinyl chloride resin, a silicone resin, a fluorine resin, an acrylic resin and a polyurethane resin, and these materials can be used alone or as a combination of two or more thereof.

The releasing member 4 consisting of a combination of two or more kinds of peel base materials 2 is constituted, for example, by laminating a silicone resin, a polyethylene film, a paper and a repositionable pressure-sensitive adhesive layer in this order.

(2) Repositionable Pressure-Sensitive Adhesive Layer and its Adhesion

The resin constituting the repositionable pressure-sensitive adhesive layer 1 in the releasing member 4 shown in FIGS. 1A and 1B is preferably a polymer consisting of a combination of two or more (meth)acrylic monomers such as 2-ethylhexyl carbitol acrylate, 2-ethylhexyl acrylate, isooctyl acrylate, dodecyl methacrylate, methyl acrylate, ethyl acrylate, n-butylacrylate, isobutyl acrylate, isoamyl acrylate, n-octyl acrylate, isononyl acrylate, 2-hydroxyethyl acrylate, 2-hydroxyethyl methacrylate, 2-hydroxypropyl acrylate, 2-hydroxypropyl methacrylate, 2-hydroxybutyl acrylate, 2-hydroxybutyl methacrylate, acrylic acid, methacrylic acid, maleic acid, crotonic acid, and β-carboxyethyl acrylate.

The glass transition point of the resin constituting the repositionable pressure-sensitive adhesive layer 1 is preferably in the range of −20 to −60° C.

This is because with such glass transition point given, the releasing member from which the sticking member has been peeled off can be easily peeled off with one hand even at a usage environment temperature in the range of low to high temperatures such as −10 to 40° C. and further because with such glass transition point given, there is less fear of deposit of the repositionable pressure-sensitive adhesive on the fixing portion to which the repositionable pressure-sensitive adhesive layer 1 adheres.

Accordingly, the glass transition point of the resin constituting the repositionable pressure-sensitive adhesive layer 1 is more preferably in the range of −25 to −55° C.

The glass transition point can be measured with a differential scanning calorimeter (DSC) or a differential thermomechanical analyzer (DTA) under known conditions, or can be calculated according to the Fox formula.

The repositionable pressure-sensitive adhesive layer 1 shown in FIGS. 1A and 1B is preferably a discontinuous layer having a lower layer exposed in the plane direction and constituted, for example, of pressure-sensitive adhesive microscopic spheres.

Figure 2:
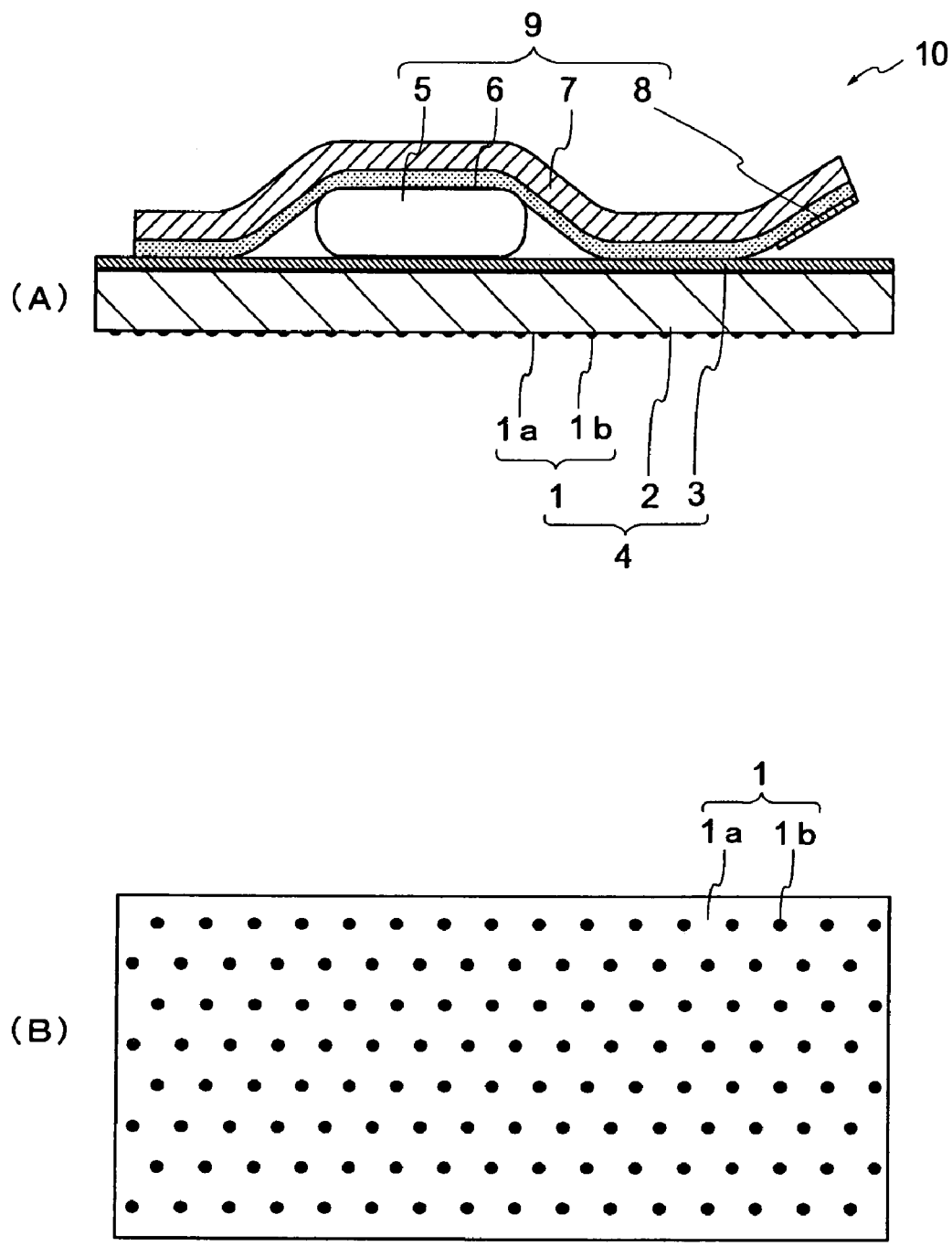
FIGS. 2A and 2B are respectively sectional and plan views of a laminated body with a releasing member having a repositionable pressure-sensitive adhesive layer that is a discontinuous layer.

As shown in FIGS. 2A and 2B, the repositionable pressure-sensitive adhesive layer 1 can be more specifically a discontinuous layer made of pressure-sensitive adhesive microscopic spheres 1b, when the laminated body 10 with a releasing member is viewed from the side of the repositionable pressure-sensitive adhesive layer.

This is because given such constitution, the releasing member 4 from which the sticking member 9 has been peeled off can be easily peeled off with one hand even in a broader range of usage environmental temperatures from low to high temperatures, while there is less fear of deposit of the repositionable pressure-sensitive adhesive on the fixing portion. Such pressure-sensitive adhesive microscopic spheres 1b can be obtained, for example, by seed polymerization or emulsion polymerization.

FIGS. 2A and 2B simultaneously show the exposed portion 1a of the releasing member 4, and preferably a primer resin layer corresponding to the exposed portion 1a is separately formed.

The resin constituting the repositionable pressure-sensitive adhesive layer 1 preferably has a crosslinked structure.

This is because a predetermined heat resistance can be conferred, while the adhesion can be easily regulated in the desired range.

The adhesion (A1), which is measured in accordance with JIS-Z-0237, of the repositionable pressure-sensitive adhesive layer 1 of the releasing member 4 shown in FIGS. 1A and 1B should be determined preferably in consideration of the adhesive (A2), which is measured in accordance with JIS-Z-0237, of the pressure-sensitive adhesive layer described later. That is, the ratio represented by A2/A1 is characterized by being a value in the range of 1.5 to 100, wherein A1 is the adhesion of the repositionable pressure-sensitive adhesive layer 1 in accordance with JIS-Z-0237 and A2 is the adhesion of the pressure-sensitive adhesive layer in accordance with JIS-Z-0237.

This is because when the ratio represented by A2/A1 is below 1.5, the sticking member 9 when peeled off from the surface of the releasing member 4 may be hardly peeled off with one hand, and because when the ratio represented by A2/A1 is above 100, the releasing member 4 from which the sticking member 9 has been peeled off may be hardly peeled off with one hand.

Accordingly, the ratio represented by A2/A1 is more preferably in the range of 5 to 80, still more preferably in the range of 8 to 50.

Figure 3:
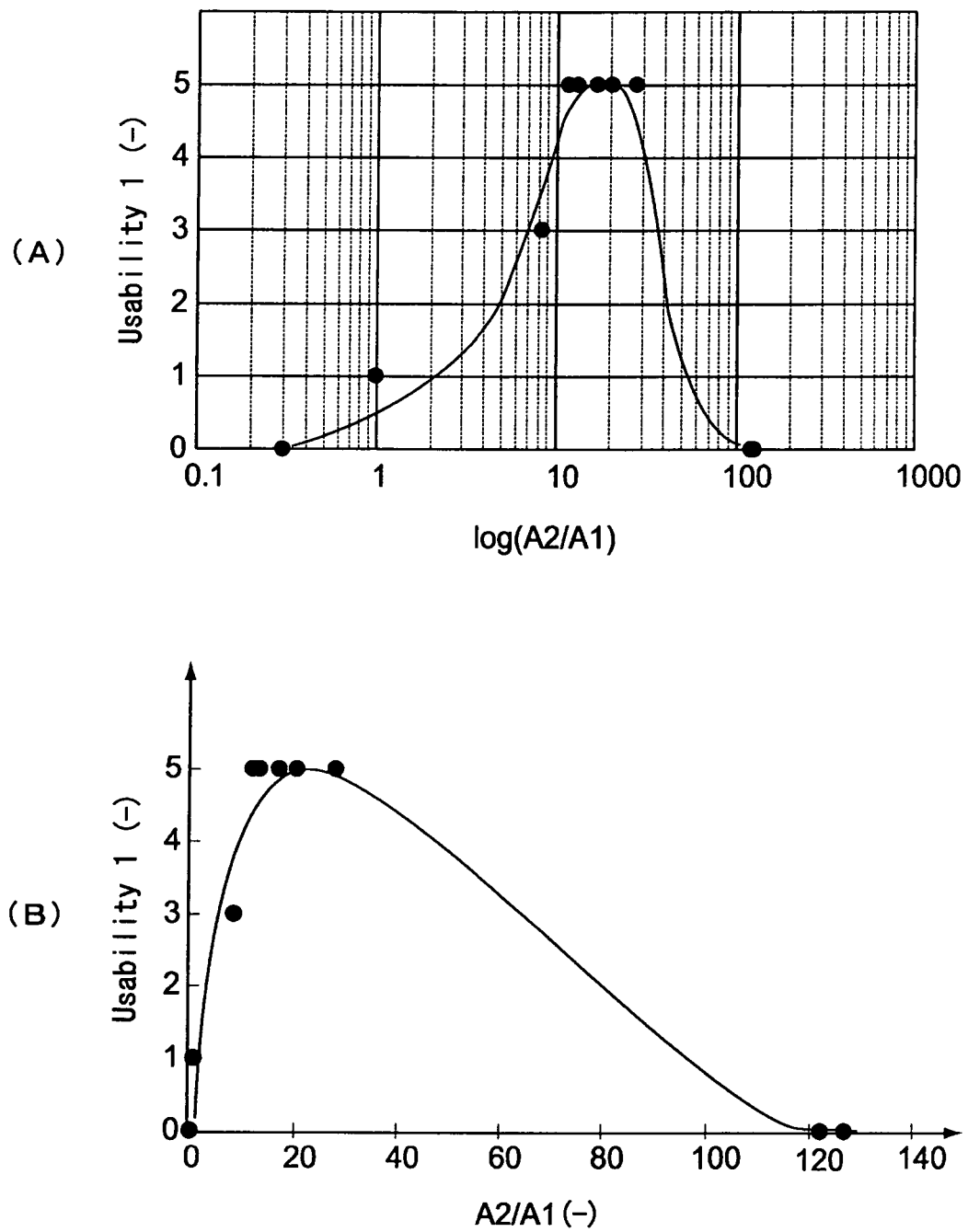
FIGS. 3A and 3B show the relationship between usability 1 and a ratio of the adhesion (A2) of a pressure-sensitive adhesive layer in accordance with JIS-Z-0237 to the adhesion (A1) of a repositionable pressure-sensitive adhesive layer in accordance with JIS-Z-0237.

FIGS. 3A and 3B shows the relationship between the ratio (–) represented by A2/A1 and usability 1 (relative value) evaluated in Example 1 etc. That is, the ratio (–) represented by A2/A1 is plotted on the abscissa, while the relative value of usability 1 evaluated by giving point 5 to Very good, point 3 to Good, point 1 to Fair, and point 0 to Bad is plotted on the ordinate. In FIG. 3A, the logarithm of the ratio represented by A2/A1 is shown on the abscissa, and in FIG. 3B, the ratio represented by A2/A1 is shown as such on the abscissa.

As can be easily seen from FIGS. 3A and 3B, the usability of the laminate becomes worse when the ratio represented by A2/A1 is either less than the predetermined value (1.5) or higher than the predetermined value (100), whereas excellent usability can be obtained when the ratio is in the predetermined range (1.5 to 100).

Specifically the adhesion (A1), in accordance with JIS-Z-0237, of the repositionable pressure-sensitive adhesive layer 1 in the releasing member 4 shown in FIGS. 1A and 1B is preferably a value in the range of 10 to 150 g/25 mm.

This is because when the adhesion (A1) is a value below 10 g/25 mm, the fixability of the laminated body 10 with a releasing member may become worse, or when the sticking member 9 is to be peeled off from the surface of the releasing member 4, the sticking member 4 may be hardly peeled off with one hand, while when the adhesion (A1) is above 150 g/25 mm, the releasing member 4 from which the sticking member 9 has been peeled off is hardly peeled off with one hand, or a part of the repositionable pressure-sensitive adhesive layer 1 may be transferred to the fixing portion.

Accordingly, the adhesion (A1), in accordance with JIS-Z-0237, of the repositionable pressure-sensitive adhesive layer 1 in the releasing member 4 is more preferably a value in the range of 20 to 100 g/25 mm, still more preferably a value in the range of 25 to 80 g/25 mm.

With respect to the position for forming the repositionable pressure-sensitive adhesive layer 1 shown in FIGS. 1A and 1B, it is preferable that as shown in FIGS. 4A and 4B, the repositionable pressure-sensitive adhesive layer 1 is formed on the other side of the releasing member 4 wholly, or wholly except for a portion along one side within 15 mm from the edge.

As shown in FIG. 4A, the repositionable pressure-sensitive adhesive layer 1 can more specifically be formed wholly when the laminated body 10 with a releasing member is viewed from the side of the repositionable pressure-sensitive adhesive layer. This is because when the repositionable pressure-sensitive adhesive layer 1 is wholly formed, the manufacturing process can be advantageously simplified.

As shown in FIG. 4B, the repositionable pressure-sensitive adhesive layer 1 can more specifically be formed partially, for example, on a part except for the portion (serving as part 2' where the repositionable pressure-sensitive adhesive layer is not formed) of the base material within 5 mm along the peripheral side, when the laminated body 10 with a releasing member is viewed from the side of the repositionable pressure-sensitive adhesive layer.

This is because when the part 2' where the repositionable pressure-sensitive adhesive layer is not formed is arranged, the part 2' facilitates release so that the sticking member when peeled off from the surface of the sticking member can be peeled off easily and reliably with one hand; and because the releasing member from which the sticking member has been peeled off can be peeled off easily and reliably with one hand; and further because even if a plurality of such laminated body with a releasing member are packaged by stacking them as they are, the laminated body can be peeled off from one another and used as individual laminated body with a releasing member.

(3) Thickness

The thickness of the releasing member 4 shown in FIGS. 1A and 1B is not particularly limited, and for example, the thickness of the releasing member containing the peel layer is preferably in the range of 10 to 200 μm.

This is because when the thickness of the releasing member 4 is below 10 μm, the mechanical characteristics may be significantly worse, and the repositionable pressure-sensitive adhesive layer 1 may be hardly formed with uniform thickness, while when the thickness of the releasing member 4 is above 200 μm, a par of the repositionable pressure-sensitive adhesive layer 1 may be transferred to the fixing portion or its production may be made difficult.

Accordingly, the thickness of the releasing member 4 is allowed to be preferably in the range of 20 to 100 μm, more preferably in the range of 25 to 50 μm.

(4) Primer Layer

Although not shown, a primer layer is preferably arranged between the peel base material 2 and the repositionable pressure-sensitive adhesive layer 1 which constitute the releasing member 4 as shown in FIGS. 1A and 1B.

This is because arrangement of such primer layer not only facilitates regulation of the adhesion (A1) of the repositionable pressure-sensitive adhesive layer but also broadens the range of choice of the type thereof. In consequence, the regulation of the adhesion (A2) of the pressure-sensitive adhesive layer is not only facilitated, but the range of choice of the type thereof is also broadened.

Although the type and thickness of the primer layer are not particularly limited, it is preferable that an epoxy-based primer resin or a urethane-based primer resin is used, while the thickness of the primer layer is preferably in the range of 0.1 to 30 μm.

2. Substrate

A base material 7 (referred to sometimes as sticking base material) constituting a part of the sticking member 9 shown in FIGS. 1A and 1B includes, but is not limited to, a paper, an impregnated paper, a polyester resin, a polycarbonate resin, a polypropylene resin, a polyethylene resin, a polyamide resin, an acrylic resin, a vinyl chloride resin, a silicone resin, a fluorine resin and a urethane resin, and these materials may be used alone or as a combination of two or more thereof.

Among these base materials, the polyester resin typified by a polyethylene terephthalate resin and a polyethylene naphthalate resin is a more excellent base material, because it is relatively inexpensive and shows excellent transparency and mechanical characteristics.

A composite base material constituted of the above base material laminated with a net is also preferable. The base material may be endowed with a decorating effect by adding a coloring agent therein or thereon or by printing.

2. Pressure-Sensitive Adhesive Layer (1) Type

A pressure-sensitive adhesive layer 6 constituting a part of the sticking member 4 shown in FIGS. 1A and 1B includes a polyester resin, a polyamide resin, an acrylic resin, a urethane resin, a vinyl chloride resin, a phenolic resin, an epoxy resin, a silicone resin and a fluorine resin, and these materials may be used alone or as a combination of two or more thereof.

Among these resins constituting the pressure-sensitive adhesive layer 6, an acrylic resin is more preferable resin because it is relatively inexpensive and may show an excellent transparency and the good mechanical characteristics.

(2) Adhesion

It is preferable that the adhesion (A2), in accordance with JIS-Z-0237, of the pressure-sensitive adhesive layer 6 shown in FIGS. 1A and 1B is specifically in the range of 250 to 1,000 g/25 mm.

This is because if the adhesion (A2) is below 250 g/25 mm, the laminated body when used, for example, as a medical adhesive plaster or as an adhesive plaster for injection may be peeled off from the skin etc., while if the adhesion (A2) is above 1,000 g/25 mm, the laminated body when peeled off from the skin may severely damage the corneum.

Accordingly, it is preferable that the adhesion (A2) of the pressure-sensitive adhesive layer 6 in accordance with JIS-Z-0237 is specifically in the range of preferably 300 to 800 g/25 mm, more preferably in the range of 400 to 600 g/25 mm.

(3) Thickness

The thickness of the pressure-sensitive adhesive layer 6 shown in FIGS. 1A and 1B is not particularly limited, and is preferably, for example, in the range of 10 to 200 μm.

This is because when the thickness of the pressure-sensitive adhesive layer 6 is below 10 μm, the mechanical characteristics may be significantly worse and the repositionable pressure-sensitive adhesive layer 1 may be hardly formed with uniform thickness, while when the thickness of the pressure-sensitive adhesive layer 6 is above 200 μm, a part of the pressure-sensitive adhesive layer 6 may be transferred onto the skin etc. or production of the laminated body is made difficult in some cases.

Accordingly, the thickness of the pressure-sensitive adhesive layer 6 is more preferably in the range of 15 to 100 μm, still more preferably in the range of 20 to 50 μm.

4. Pad

Preferably, a pad is laminated on the pressure-sensitive adhesive layer. This is because the laminated body when used as a medical adhesive plaster or as an adhesive plaster for injection can effectively exhibit a liquid absorption effect on blood etc. and further because suitable cushioning properties can be obtained by laminating such pad on the pressure-sensitive adhesive layer.

The shape of the pad is not particularly limited, and for example, it is preferable that the thickness is in the range of 0.1 to 1 mm, and the area is in the range of 1 to 1000 mm$^2$.

5. Shape

The shape of the laminated body with a releasing member can be suitably changed depending on applications, and for example, the laminated body is preferably shaped as shown in embodiments in FIGS. 5A to 5D, FIGS. 6A to 6C, or FIGS. 7A to 7D.

Figure 5:
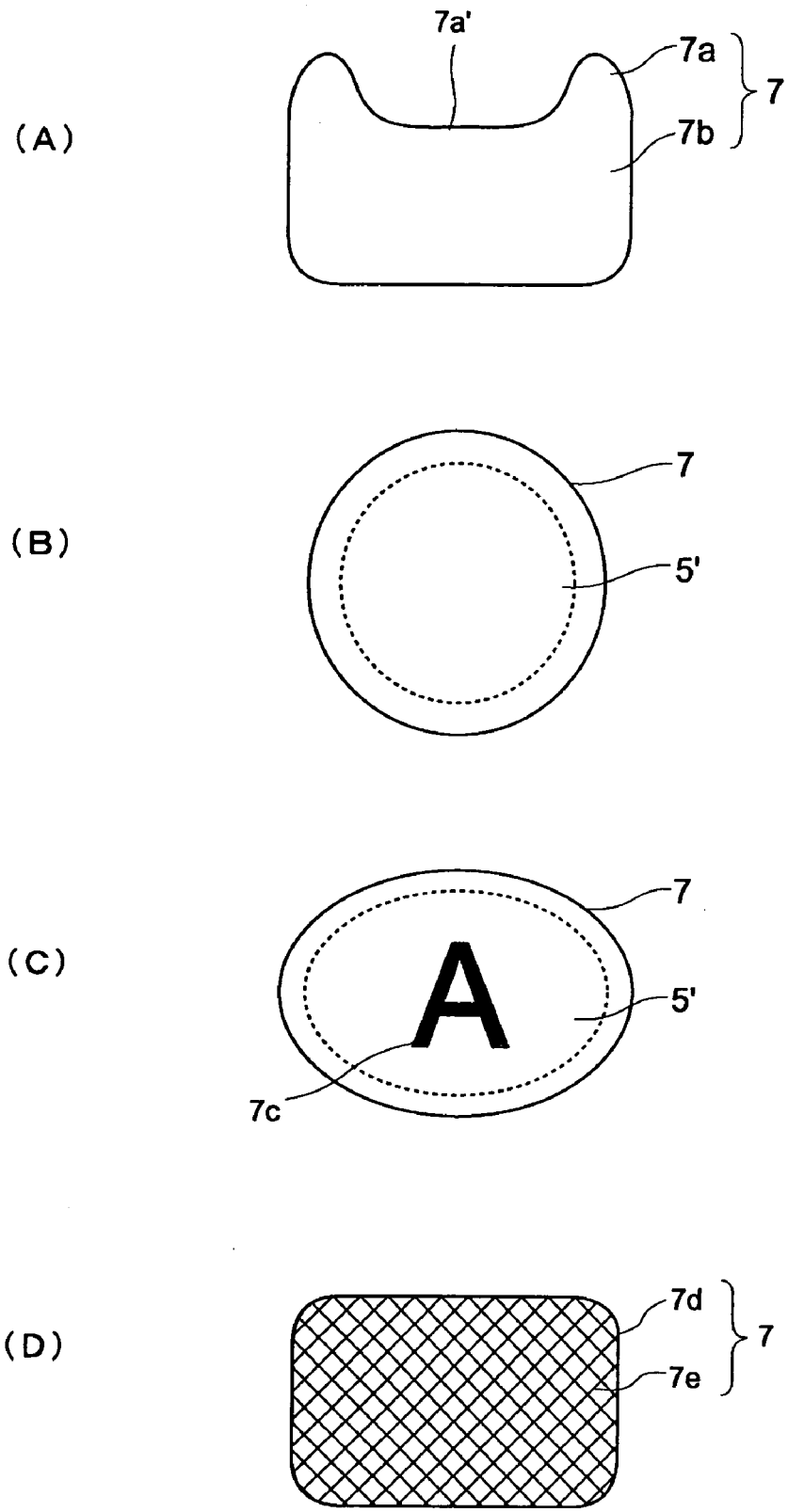
FIGS. 5A to 5D show a modification (No. 1) of the laminated body with a releasing member according to the present invention.

First, FIG. 5A shows a laminated body with a releasing member, which is formed approximately in the shape of U-letter as a whole by arranging protrusions 7a in both ends of one side of the base material 7. With this configuration given, the laminated body can be fitted and stuck to a boundary between the finger nail and skin and can be provided preferably as a tape for protecting an inverted nail, etc.

FIG. 5B shows a laminated body with a releasing member wherein the base material 7 has a circular periphery and the position of the pad 5 at the backside is expressed by dotted line 5'. With this configuration given, the laminated body can be provided preferably as a nip-less tape or the like.

FIG. 5C shows a laminated body with a releasing member wherein the base material 7 has an elliptical periphery, the position of the pad 5 at the backside is expressed by dotted line 5', and latter A is formed on the surface of the base material 7. With this configuration given, the laminated body can be provided preferably as, for example, a tape with a character aimed at children.

FIG. 5D shows a laminated body with a releasing member wherein a net member 7e is integrated in the surface or inside of the base material 7. With this configuration given, the laminated body can be provided preferably as a medical tape, an industrial tape or the like with the base material 7 having strength, flexibility and heat resistance improved by suitably changing the net member 7e.

FIG. 6A shows a laminated body with a releasing member wherein a circular protrusion 7f is arranged on one side of the base material 7, and cuttings 7g are arranged aslant in the circular protrusion 7f.

FIG. 6B shows a laminated body with a releasing member provided with a large number of cuttings 7g, which is a modification of the laminated body with a releasing member shown in FIG. 6A.

With these configurations given, the laminated body can be stuck closely to and around the finger including the nail and can be provided preferably as a medical tape, an inverted finger-protecting tape or the like.

FIG. 7A shows a laminated body 7 with a releasing member wherein a changeover part 7h is arranged in the middle of the side of the base material 7 to change the size (area) of the base above and below the part 7h. With this configuration given, the base above the changeover part 7h can be first wound around a part of the finger and then the base below the changeover part 7h can be wound around the finger. Accordingly, the laminated body can be provided preferably as a medical tape or the like excellent in usability and fixability.

FIG. 7B shows a laminated body 7 with a releasing member formed as a whole in the form of approximately butterfly wherein a changeover part 7i is arranged in the middle of the side of the base material 7 such that the size (area) of the base above the part 7i is made identical with that below the part 7i. With this configuration given, a pad 5' on the changeover part 7i is attached to a wound, and then the base above the changeover part 7i and the base below the changeover part 7i can be alternately wound around the wound. Accordingly, the laminated body can be provided preferably as a medical tape or the like excellent in usability and fixability.

FIG. 7C shows a laminated body 7 with a releasing member wherein cutouts or different-material portions 7j are arranged in the middle of the side of the base material 7. With this configuration given, the laminated body regardless of whether it is wound around the finger etc. or stuck to the skin can be provided preferably as a medical tape or the like which is excellent in usability and fixability due to the function of the cutouts or different-material portions 7j.

FIG. 7D shows a laminated body 7 with a releasing member wherein protrusions 7k and 7l different in size from each other are arranged in the upper and lower sides of the base material 7, which is a modification of the laminated body with a releasing member shown in FIG. 7A. With this configuration given, the laminated body can be provided preferably as a medical tape or the like which is excellent in usability and fixability.

Figure 8:
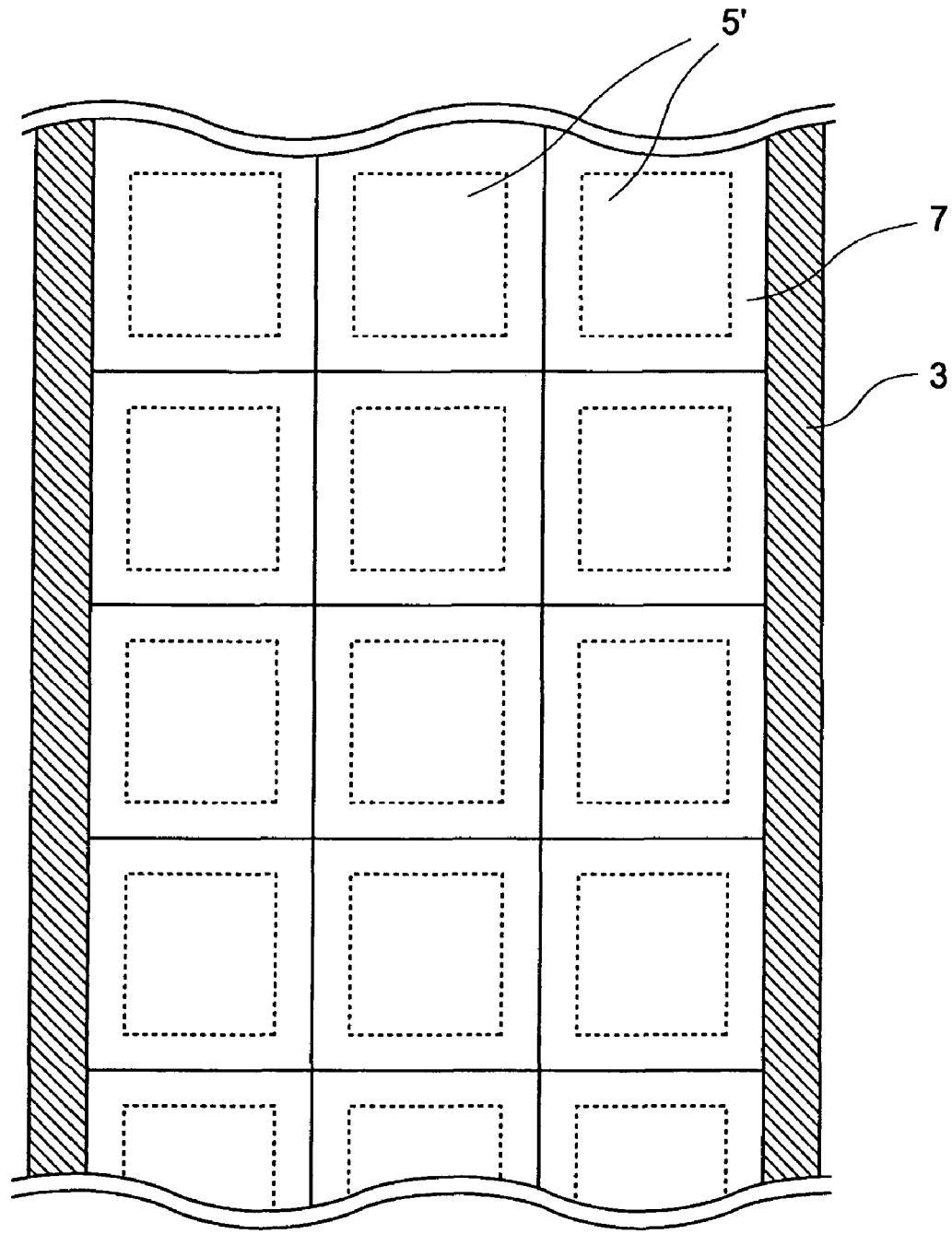
FIG. 8 shows a modification (No. 4) of the laminated body with a releasing member according to the present invention.

FIG. 8 shows a set of laminated body with a releasing member (laminated body, for example, in at least 3 horizontal rows and at least 5 vertical rows) arranged on a releasing member 3 on which the repositionable pressure-sensitive adhesive layer larger in area than the set of laminated body has been formed.

With this configuration given, the releasing member 3 on which the relatively large repositionable pressure-sensitive adhesive layer has been formed, and the relatively small laminated body with a releasing member, can be more easily peeled off from each other, so the laminated body may be used as a medical adhesive plaster or an adhesive plaster for injection excellent in usability.

Second Embodiment

A second embodiment is a method for manufacturing a laminated body with a releasing member, which includes a sticking member constituted by sequentially laminating a base material and a pressure-sensitive adhesive layer, a releasing member being laminated on the side of the sticking member that is provided with the pressure-sensitive adhesive layer, and a repositionable pressure-sensitive adhesive layer being formed as a part of the releasing member at the backside of the releasing member, the method including the steps:

forming a repositionable pressure-sensitive adhesive layer on one side of the releasing member; and laminating a base material and a pressure-sensitive adhesive on the other side of the releasing member, wherein a ratio represented by A2/A1 is allowed to be in the range of 1.5 to 100 where A1 is the adhesion of the repositionable pressure-sensitive adhesive layer in accordance with JIS-Z-0237 and A2 is the adhesion of the pressure-sensitive adhesive layer in accordance with JIS-Z-0237. That is, such a manufacturing method can be carried out by a manufacturing apparatus 80 shown in FIG. 9. Thus, the second embodiment is described in more detail with reference to FIGS. 1 and 9 to 12.

1. Step of Forming Releasing Member (Step of Forming Repositionable Pressure-Sensitive Adhesive Layer)

As constituent resin constituting the repositionable pressure-sensitive adhesive layer 1 shown in FIG. 1, a repositionable pressure-sensitive adhesive (pressure-sensitive adhesive microscopic spheres) made of a (meth)acrylic copolymer having a weight-average molecular weight of 100,000 to 1,000,000 is synthesized, for example, under the conditions of 50 to 90° C. and 3 to 48 hours by known emulsion polymerization.

Then, the resultant repositionable pressure-sensitive adhesive made of a (meth) acrylic copolymer is laminated on one side (backside) of a peel base material 2 constituting a part of a releasing member to form the repositionable pressure-sensitive adhesive layer 1. That is, as shown in FIGS. 10A to 10C, the repositionable pressure-sensitive adhesive layer 1 made of the repositionable pressure-sensitive adhesive is formed by using a publicly known applicator 100 such as a knife coater or a roll coater and then dried to form a releasing member 4 having the repositionable pressure-sensitive adhesive layer 1.

Figure 9:
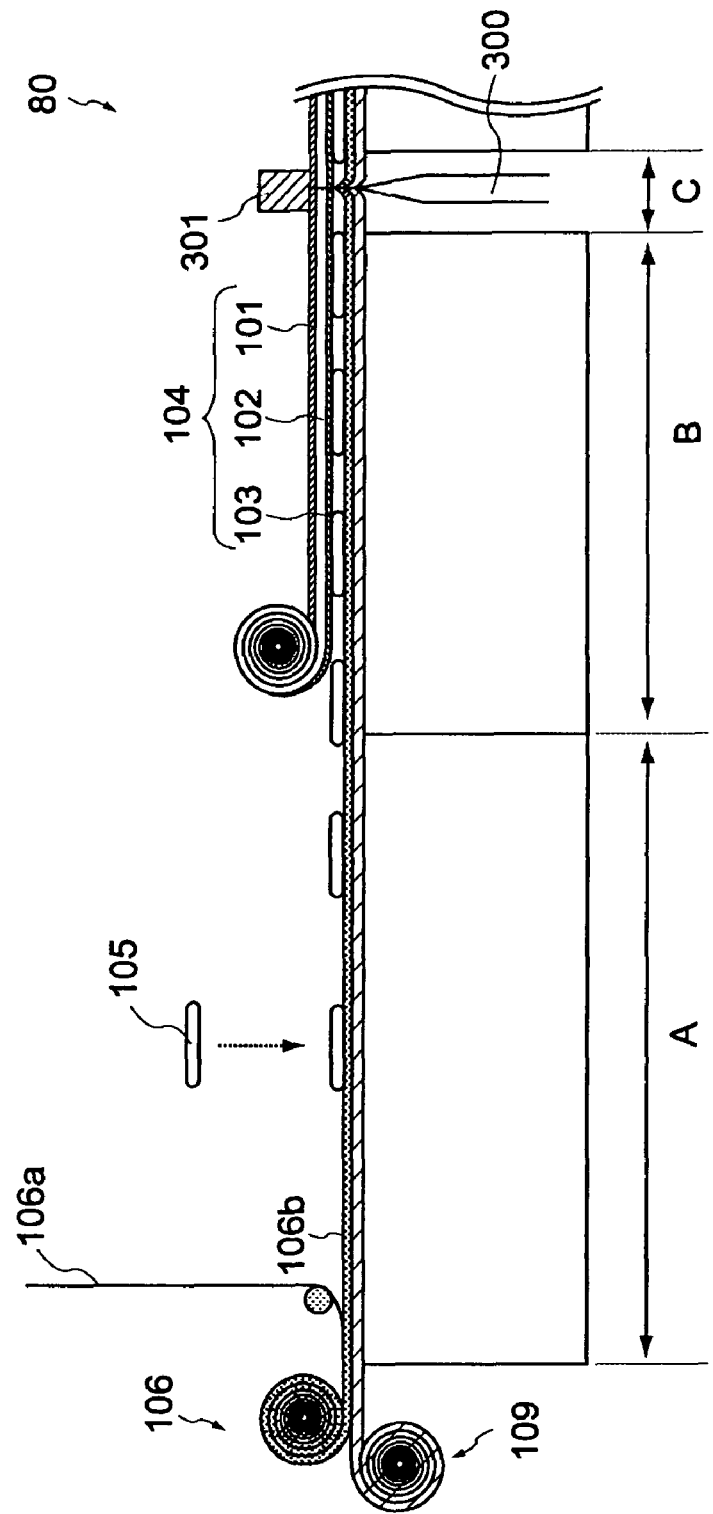
FIG. 9 is a view explaining a method for manufacturing a laminated body with a releasing member according to the present invention.
Figure 10:
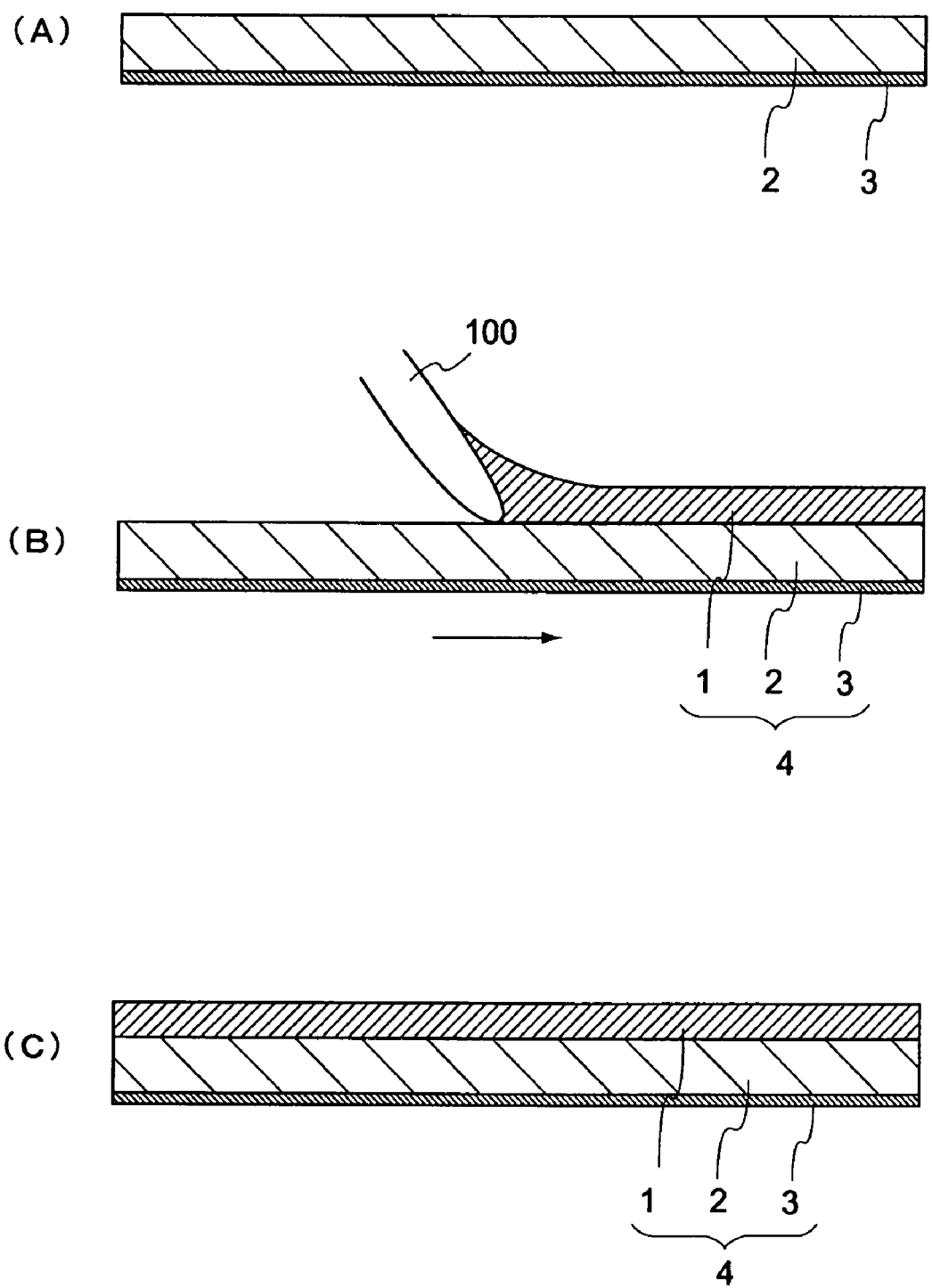
FIGS. 10A to 10C are views explaining a method for manufacturing a releasing member.
Figure 11:
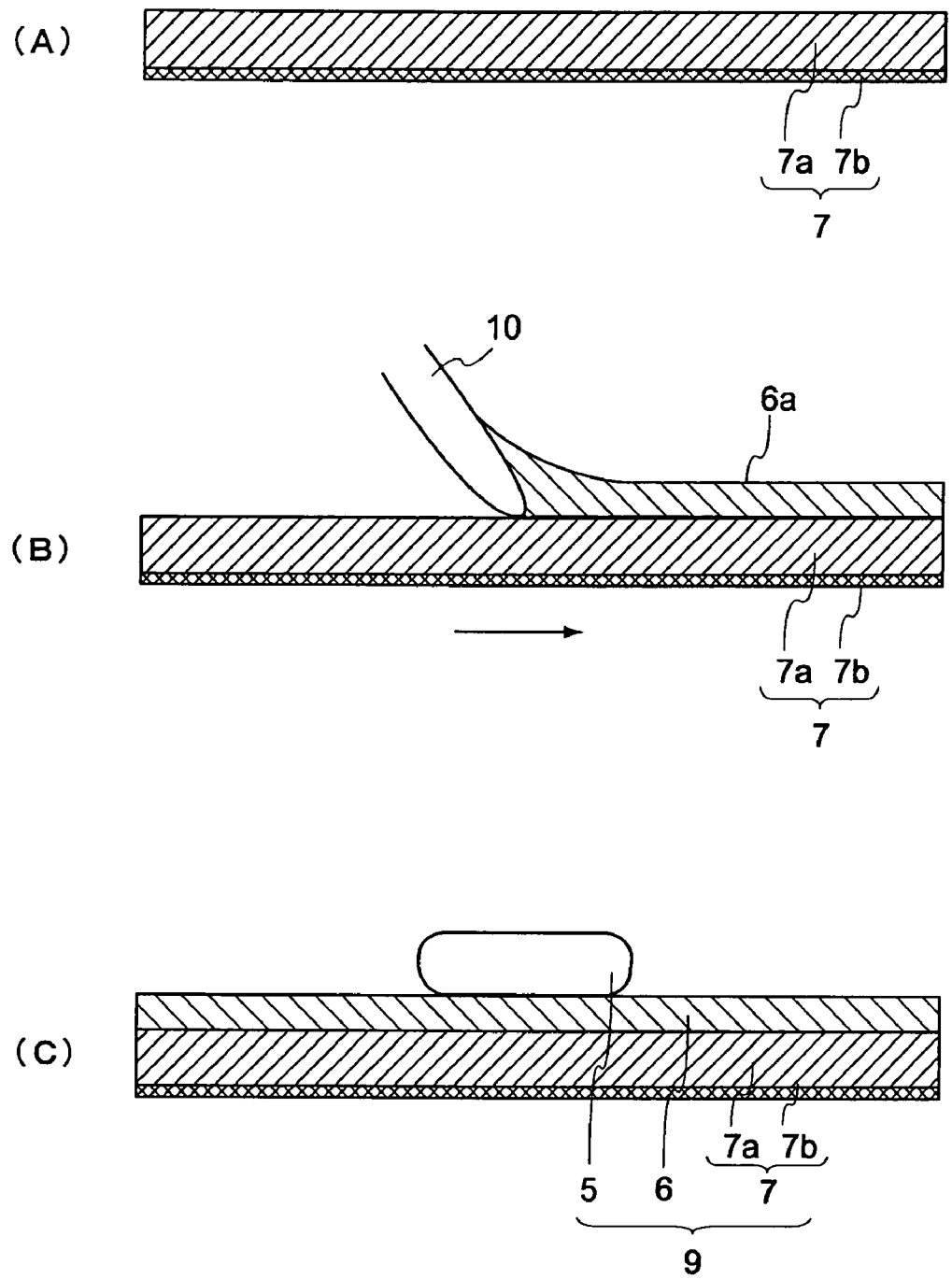
FIGS. 11A to 11C are views explaining a method for manufacturing a sticking member.
Figure 12:
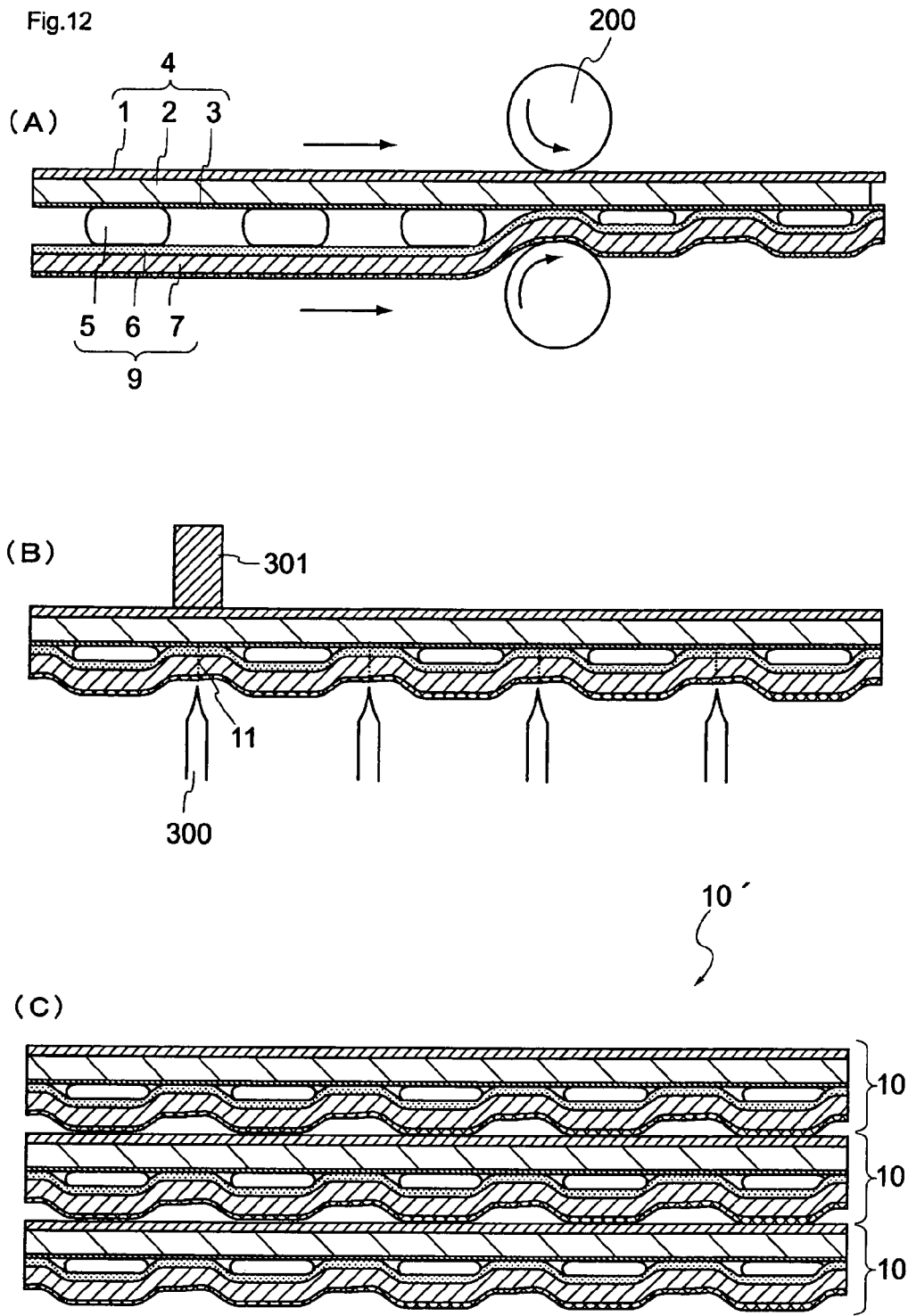
FIGS. 12A to 12C are views explaining a step of laminating a releasing member with a sticking member, a step of cutting a laminated body with a releasing member, and a cutting step according to the present invention, respectively.
Figure 13:
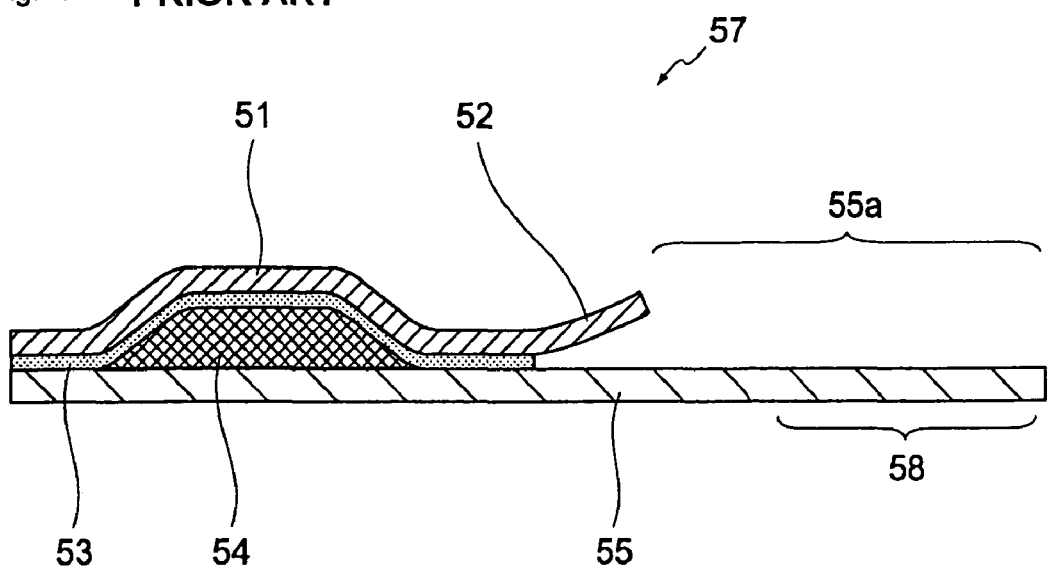
FIG. 13 shows a conventional adhesive plaster for injection.
Figure 14:
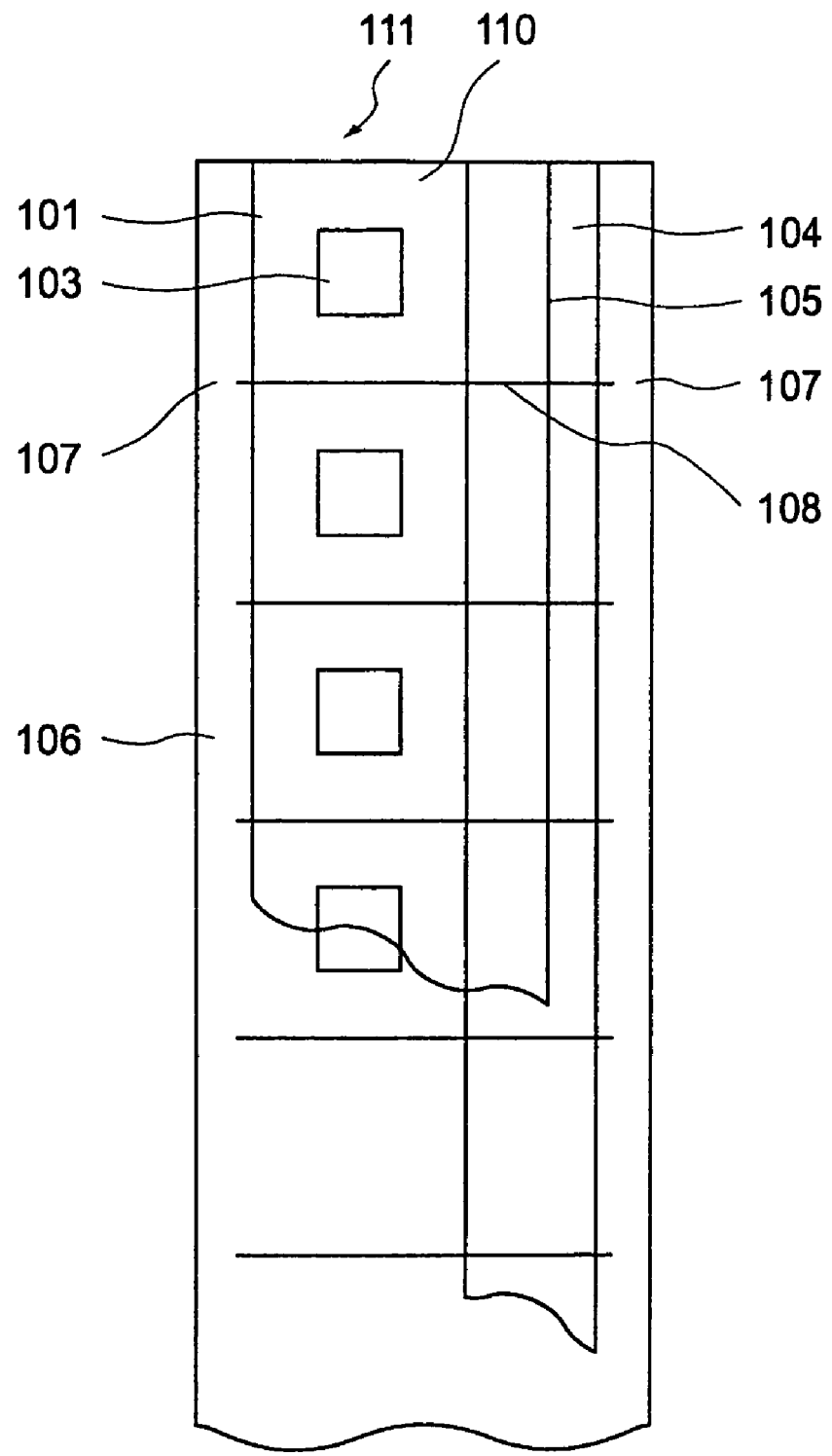
FIG. 14 shows a conventional medical adhesive plaster.

The resultant releasing member 4 having the repositionable pressure-sensitive adhesive layer 1 is arranged as a roll releasing member 104 at the position in step C in FIG. 9 to produce a laminated body 10 with a releasing member.

2. Step of Laminating Base Material and Pressure-Sensitive Adhesive Layer (Step of Forming Sticking Member)

On the other hand, a base material 7 constituting a part of a sticking member 9 shown in FIG. 1 is prepared, and a pressure-sensitive adhesive layer 6 is formed on the surface of the base material 7. That is, as shown in FIG. 11A, a base material 7 constituted of a film base material 7a and a releasing layer 7b is prepared. Then, as shown in FIG. 11B, a pressure-sensitive adhesive layer 1 made of an acrylic pressure-sensitive adhesive etc. is formed on the surface of the film base material 7a by using a known applicator 100 such as a knife coater or a roll coater and then dried to form a pressure-sensitive adhesive layer 6. Finally, as shown in FIG. 11C, a pad 5 for exhibiting a liquid absorption effect on blood etc. is laminated on the surface of the pressure-sensitive adhesive layer 6, in the case of a medical adhesive plaster or an adhesive plaster for injection.

The sticking member 9 formed in this manner is arranged as a roll-shaped sticking member 109 at the position in step A in FIG. 9 to produce a laminated body 10 with a releasing member.

3. Step of Laminating Sticking Member and Releasing Member

The sticking member 9 shown in FIG. 1 and the releasing member 4 are then laminated into a lengthy product. That is, as shown in FIG. 12A, the sticking member 9 and the releasing member 4 are laminated under the laminating conditions of, for example, room temperature (25° C.), 0.1 to 20 kgf/cm (linear pressure) and 0.05 to 60 seconds with a pressing device 200 such as a laminator to form a lengthy product having, for example, a length of 100 m and a width of 0.5 m. Such a lamination step can be carried out in step B in FIG. 9 in order to produce a laminated body 10 with a releasing member. The lamination step is also preferably carried out simultaneously with a cutting step described later.

If necessary, a picking piece is preferably arranged between the releasing member and the sticking member, during or before the step of laminating the sticking member with the releasing member.

This is because when the laminated body is constituted by arranging a picking piece, the usability of the laminated body is improved, and as a result, it is possible to broaden the ratio (A2/A1) of the adhesion (A1) of the repositionable pressure-sensitive adhesive layer in accordance with JIS-Z-0237 to the adhesion (A2) of the pressure-sensitive adhesive layer in accordance with JIS-Z-0237. Accordingly, the resultant laminated body can be provided more preferably as a medical adhesive plaster or an adhesive plaster for injection, while production conditions can be relaxed.

4. Cutting Step

Then, the resultant lengthy product including the sticking member 9 and the releasing member 4 is provided with a cutting line. That is, as shown in FIG. 12B, the lengthy product is provided, for example, with a straight or dotted cutting line 11 of 0.1 to 0.3 mm in width by a cutting device 300 such as a cutter.

Such a cutting step can be carried out in step C in FIG. 9 in producing the laminated body 10 with a releasing member.

5. Packaging Step

A plurality of laminated body with a releasing member such as 2 to 10 sheets, can be stacked as they are, and then packaged by covering the resultant stack with a polyethylene-impregnated paper or the like.

That is, as shown in FIG. 12C, a stack 10' of laminated body with a releasing member is formed and then covered by a packaging apparatus (not shown) with a polyethylene-impregnated paper or the like on and around the stack 10' of laminated body with a releasing member.

Such a cutting step is not shown in FIG. 9 showing production of the laminated body 10 with a releasing member, but can be carried out after step C.

EXAMPLES

Hereinafter, the present invention is described in more detail by reference to the Examples. As a matter of course, the scope of the invention is not limited to the following description.

Example 1

1. Production of the Laminated Body with a Releasing Member (1) Step of Preparing Releasing Member 1 part by weight of Aqualon HS-10, 3 parts by weight of Aqualon RN-20, and 1 part by weight of sodium p-styrenesulfonate were added as surfactants to 100 parts by weight of deionized water kept in a stirring container, and 2 parts by weight of diacetone acrylamide was further added to the mixture to prepare a uniform solution.

Then, 83 parts by weight of 2-ethylhexyl carbitol acrylate, 8 parts by weight of nonyl phenoxy polyethylene glycol acrylate, 2 parts by weight of acrylic acid and 2.5 parts by weight of stearyl acrylate were added to the stirring container.

Then, the mixture was stirred under the condition of 15,000 rpm for 15 minutes with a high-speed rotating stirrer manufactured by Tokushu Kika Kogyo Co., Ltd. to prepare an emulsified dispersion.

The resultant emulsified dispersion was introduced into a reactor equipped with a stirrer, a reflux condenser, a thermometer and a nitrogen gas inlet, and 0.2 parts by weight of ammonium persulfate was charged as a polymerization initiator. While a nitrogen gas was purged, the emulsion polymerization reaction was carried under the conditions of 65° C. and 5 hours to prepare an acrylic copolymer having a weight-average molecular weight of about 1,200,000 and a glass transition point of about −30° C.

(2) Step of Forming a Repositionable Pressure-Sensitive Adhesive layer

As shown in FIG. 10A, an acrylic copolymer 1a was then laminated on the backside of a peel base material 2a made of a paper laminated with a polyethylene film of 25 μm in thickness having a silicone peel layer 3a formed thereon. That is, as shown in FIGS. 10B and 10C, the acrylic copolymer 1a was laminated by a knife coater 100 such that the thickness thereof after drying became 25 μm, thereby obtaining a releasing member 4a having the silicone peel layer 3a on the surface and the repositionable pressure-sensitive adhesive layer 1 on the backside.

(3) Step of Laminating a Base Material and a Pressure-Sensitive Adhesive Layer

Then, a pressure-sensitive adhesive layer made of an acrylic pressure-sensitive adhesive was formed on the backside of a sticking base material having a peel layer. That is, as shown in FIG. 11A, a sticking base material 7c made of a polyethylene film of 25 μm in thickness having a silicone releasing layer 7b formed on one side thereof was prepared.

As shown in FIG. 11B, a pressure-sensitive adhesive layer 6a made of a commercial acrylic pressure-sensitive adhesive having a weight-average molecular weight of about 700,000 and a glass transition point of −25° C. was then formed by a knife coater 100 such that the thickness of the layer after drying became 50 μm.

As shown in FIG. 11C, a pad 5a was then laminated on the pressure-sensitive adhesive layer to form a sticking member 9a.

(4) Step of Laminating the Sticking Member with a Releasing Member

As shown in FIG. 12A, the sticking member 9a and the releasing member 4a were then laminated into a lengthy product. That is, the sticking member 9a and the releasing member 4a were laminated under the conditions of room temperature (25° C.), 10 kgf/cm (linear pressure) and 3 seconds with a pressing device 200 such as a laminator, to form a lengthy product having a length of 100 m and a width of 0.5 m.

(5) Cutting Step

Then, the resultant lengthy product was provided with a cutting line as shown in FIG. 12B. That is, a cutter 300 was used to provide a cutting line 11 having a width of 0.1 mm.

(6) Packaging Step

As shown in FIG. 12C, three laminated bodies 10 with a releasing member were stacked, as they were in one direction to prepare a stack 10' of the laminated body with a releasing member. Then, a packaging apparatus (not shown) was used to cover the stack thereon and therearound with a polyethylene-impregnated paper thereby sealing the stack, whereby a stack of the laminated body with a releasing member in Example 1 was obtained.

2. Evaluation of the Laminated Body with a Releasing Member (1) Usability 1

The usability (1) of the resultant laminated body with a releasing member was evaluated under the following criteria. Such usability (1) was determined by sticking 5 sample pieces to a base material (wooden table) for 1 hour and then evaluating each piece under the following criteria. The results obtained are shown in Table 1.

Very good: For all 5 samples, the laminated body only can be peeled off with one hand.
Good: For 4 of 5 samples, the laminated body only can be peeled off with one hand.
Fair: For 3 of 5 samples, the laminated body only can be peeled off with one hand.
Bad: For 2 or less of 5 samples, the laminated body only can be peeled off with one hand.

(2) Usability 2

The usability (2) of the resultant laminated body with a releasing member was evaluated under the following criteria. Such usability (2) was determined by evaluating the handling ability (removability from a wooden table) of the releasing member from which the sticking member had been peeled off in evaluation of the usability (1), and then evaluating each sample under the following criteria. The results obtained are shown in Table 1.

Very good: For all 5 samples, the releasing member can be peeled off from the wooden table with one hand.
Good: For 4 of 5 samples, the releasing member can be peeled off from the wooden table with one hand.
Fair: For 3 of 5 samples, the releasing member can be peeled off from the wooden table with one hand.
Bad: For 2 or less of 5 samples, the releasing member can be peeled off from the wooden table with one hand.

(3) Cutting Property

The cutting property of the laminated body with a releasing member was evaluated under the following criteria. Such cutting property was determined by cutting 5 sample pieces with a cutter and evaluating each piece. The results obtained are shown in Table 1.

Very good: All 5 samples can be processed with dimensional accuracy±0.5 mm.
Good: All 5 samples can be processed with dimensional accuracy±1 mm.
Fair: All 5 samples can be processed with dimensional accuracy±3 mm.
Bad: All 5 samples cannot be processed with dimensional accuracy±3 mm.

(4) Packaging Property

The resultant laminated body with a releasing member after packaging was heated at 40° C. for 1 week, and then its packaging property was evaluated under the following criteria. Such packaging property was determined by evaluating 5 laminated bodies with a releasing member after packaging. The results obtained are shown in Table 1.

Very good: All 5 sheets can be easily peeled off with one hand.
Good: 4 of 5 sheets can be easily peeled off with one hand.
Fair: 3 of 5 sheets can be easily peeled off with one hand.
Bad: 2 or less of 5 sheets can be easily peeled off with one hand.

Examples 2 to 5

In Examples 2 to 5, the laminated body with a releasing member were prepared and evaluated respectively in the same manner as in Example 1 except that a phthalic acid-based plasticizer was added to each of the resins constituting the repositionable pressure-sensitive adhesive layer and the pressure-sensitive adhesive layer in Example 1 and the type of the pressure-sensitive adhesive was changed to thereby change the adhesion (A2) of the pressure-sensitive adhesive layer.

Comparative Examples 1 to 4

In Comparative Examples 1 to 4, the laminated body with a releasing member were prepared and evaluated respectively in the same manner as in Example 1 except that the type of each of the resin constituting the repositionable pressure-sensitive adhesive layer and the pressure-sensitive adhesive layer was changed (and a plasticizer was added) to thereby change the adhesion (A1) of the repositionable pressure-sensitive adhesive layer and the adhesion (A2) of the pressure-sensitive adhesive layer, respectively.

TABLE 1

|  | Adhesion (A1) | Adhesion (A2) | Adhesion ratio (A2/A1) | Usability 1 | Usability 2 | Cutting property | Packaging property |
| --- | --- | --- | --- | --- | --- | --- | --- |
| Example 1 | 30 | 264 | 8.4 | Fair | Very good | Very good | Very good |
| Example 2 | 30 | 354 | 11.8 | Good | Very good | Very good | Very good |
| Example 3 | 30 | 405 | 13.3 | Very good | Very good | Very good | Very good |
| Example 4 | 30 | 503 | 16.8 | Very good | Very good | Very good | Very good |
| Example 5 | 30 | 610 | 20.3 | Very good | Very good | Very good | Very good |
| Example 6 | 30 | 840 | 28 | Very good | Very good | Very good | Very good |
| Comparative Example 1 | 5 | 610 | 122 | Bad | Very good | Very good | Very good |
| Comparative Example 2 | 10 | 1270 | 127 | Bad | Very good | Very good | Fair |
| Comparative Example 3 | 50 | 50 | 1 | Fair | Good | Very good | Fair |
| Comparative Example 4 | 400 | 120 | 0.3 | Bad | Bad | Bad | Bad |

* Unit of adhesion (A1) and (A2) is g/25 mm.

According to the laminated body with a releasing member according to the present invention and a method for manufacturing the same, the following advantage is given. The adhesion (A1) of the repositionable pressure-sensitive adhesive layer and the adhesion (A2) of the pressure-sensitive adhesive layer are related to each other, so that when the sticking member is peeled off from the surface of the releasing member, the releasing member can be easily peeled off with one hand, while the releasing member from which the sticking member has been peeled off can also be easily peeled off with one hand.

Even if a plurality of such laminated body with a releasing member are packaged by stacking them as they are, the laminated body can be easily peeled off from one another and used as individual laminated body with a releasing member.

According to the present invention, there can be efficiently provided a laminated body with a releasing member not only excellent in usability but also excellent in packaging property and cutting property, as well as a method for manufacturing the same.

What is claimed is:

1. A medical laminated body with a releasing member, which comprises:
   a medical sticking member comprising a sequentially laminated base material and a pressure-sensitive adhesive layer,
   a releasing member laminated on a side of the medical sticking member that is provided with the pressure-sensitive adhesive layer, and
   a repositionable pressure-sensitive adhesive layer formed as a part of the releasing member at a side of the releasing member distal from the medical sticking member,
   wherein a ratio represented by A2/A1 is in a range of 8 to 100 where A1 is an adhesion of the repositionable pressure-sensitive adhesive layer in accordance with JIS-Z-0237 and A2 is an adhesion of the pressure-sensitive adhesive layer in accordance with JIS-Z-0237,
   A1 is in the range of 10 to 150 g/25 mm, and
   A2 is in the range of 250 to 1,000 g/25 mm.

2. The medical laminated body with a releasing member according to claim 1, wherein the repositionable pressure-sensitive adhesive layer is formed wholly or partially on the side of the releasing member distal from the medical sticking member.

3. The medical laminated body with a releasing member according to claim 1, wherein a fluid absorbing pad portion is arranged on the surface of the pressure-sensitive adhesive layer in the sticking member.

4. The medical laminated body with a releasing member according to claim 3, wherein the fluid is a bodily fluid.

5. The medical laminated body with a releasing member according to claim 3, wherein the fluid is blood.

6. The medical laminated body with a releasing member according to claim 1, wherein a glass transition point of a repositionable pressure-sensitive adhesive constituting the repositionable pressure-sensitive adhesive layer is in the range of −20 to −60° C.

7. The medical laminated body with a releasing member according to claim 1, wherein the repositionable pressure-sensitive adhesive layer is a discontinuous layer with a lower exposed surface.

8. The medical laminated body with a releasing member according to claim 1, wherein a primer layer is arranged between the repositionable pressure-sensitive adhesive layer and the releasing member.

9. The medical laminated body with a releasing member according to claim 1, wherein a picking piece is arranged between the releasing member and the sticking member.

10. The medical laminated body with a releasing member according to claim 1, wherein the base material is provided with a cutting line along which the base material is cut in a predetermined shape.

11. The medical laminated body with a releasing member according to claim 1, wherein the pressure sensitive adhesion layer is adapted to be disposed on skin.

12. The medical laminated body with a releasing member according to claim 1, wherein the adhesion (A2) has a property such that when the adhesion (A2) is in the range of 250 to 1000 g/25 mm, the pressure-sensitive adhesive layer is peeled off skin, while when the adhesion (A2) is above 1,000 g/25 mm, the pressure-sensitive adhesive layer when peeled off from the skin severely damages a corneum of the skin.

13. A method for manufacturing a medical laminated body with a releasing member, which comprises a medical sticking member formed by sequentially laminating a base material and a pressure-sensitive adhesive layer, a releasing member laminated on a side of the medical sticking member that is provided with the pressure-sensitive adhesive layer, and a repositionable pressure-sensitive adhesive layer formed as a part of the releasing member at a side of the releasing member distal from the medical sticking member, the method comprising the steps:
   forming the repositionable pressure-sensitive adhesive layer on one side of the releasing member; and
   laminating the base material and the pressure-sensitive adhesive on the other side of the releasing member,
   wherein a ratio represented by A2/A1 is in a range of 8 to 100 where A1 is an adhesion of the repositionable pressure-sensitive adhesive layer in accordance with JIS-Z-0237 and A2 is an adhesion of the pressure-sensitive adhesive layer in accordance with JIS-Z-0237,
   A1 is in the range of 10 to 150 g/25 mm, and
   A2 is in the range of 250 to 1,000 g/25 mm.

* * * * *